United States Patent
Kese et al.

[11] Patent Number: 6,024,744
[45] Date of Patent: Feb. 15, 2000

[54] COMBINED BIPOLAR SCISSOR AND GRASPER

[75] Inventors: Kelly Kese, Seattle, Wash.; Donald W. Regula, Belle Mead, N.J.

[73] Assignee: Ethicon, Inc., Somerville, N.J.

[21] Appl. No.: 08/919,432

[22] Filed: Aug. 27, 1997

[51] Int. Cl.[7] .................................................. A61B 17/39
[52] U.S. Cl. ............................................... 606/51; 606/45
[58] Field of Search ................... 606/46, 48–52, 606/205–207

[56] References Cited

U.S. PATENT DOCUMENTS

| | | |
|---|---|---|
| 4,949,717 | 8/1990 | Shaw . |
| 5,234,453 | 8/1993 | Smith et al. ............................ 606/170 |
| 5,290,287 | 3/1994 | Boebel et al. . |
| 5,342,381 | 8/1994 | Tidemand . |
| 5,396,900 | 3/1995 | Slater et al. ............................ 600/564 |
| 5,439,471 | 8/1995 | Kerr . |
| 5,445,638 | 8/1995 | Rydell et al. . |
| 5,456,684 | 10/1995 | Schmidt et al. . |
| 5,484,436 | 1/1996 | Eggers et al. ............................ 606/48 |
| 5,540,685 | 7/1996 | Parins et al. ............................ 606/51 |
| 5,700,261 | 12/1997 | Brinkerhoff ............................. 606/41 |
| 5,743,906 | 4/1998 | Parins et al. ............................ 606/51 |
| 5,766,170 | 6/1998 | Eggers .................................... 606/48 |
| 5,797,958 | 8/1998 | Yoon . |
| 5,827,281 | 11/1998 | Levin ..................................... 606/51 |

*Primary Examiner*—Linda C. M. Dvorak
*Assistant Examiner*—Roy Gibson
*Attorney, Agent, or Firm*—Scully Scott Murphy & Presser

[57] ABSTRACT

Open surgery and endoscopic versions of a combined bipolar electrosurgical cutting and grasping instrument where the grasping surfaces are contained within the shape of a standard surgical scissor. This unique arrangement results in a combined scissor and grasper which has the feel of a standard scissor but which allows surgeons to cauterize tissue and vessels while both cutting and grasping thus making the instruments well suited to perform coaptation of vessels. Also disclosed herein, are methods for using the various combined electrosurgical cutting and grasping instruments.

53 Claims, 12 Drawing Sheets

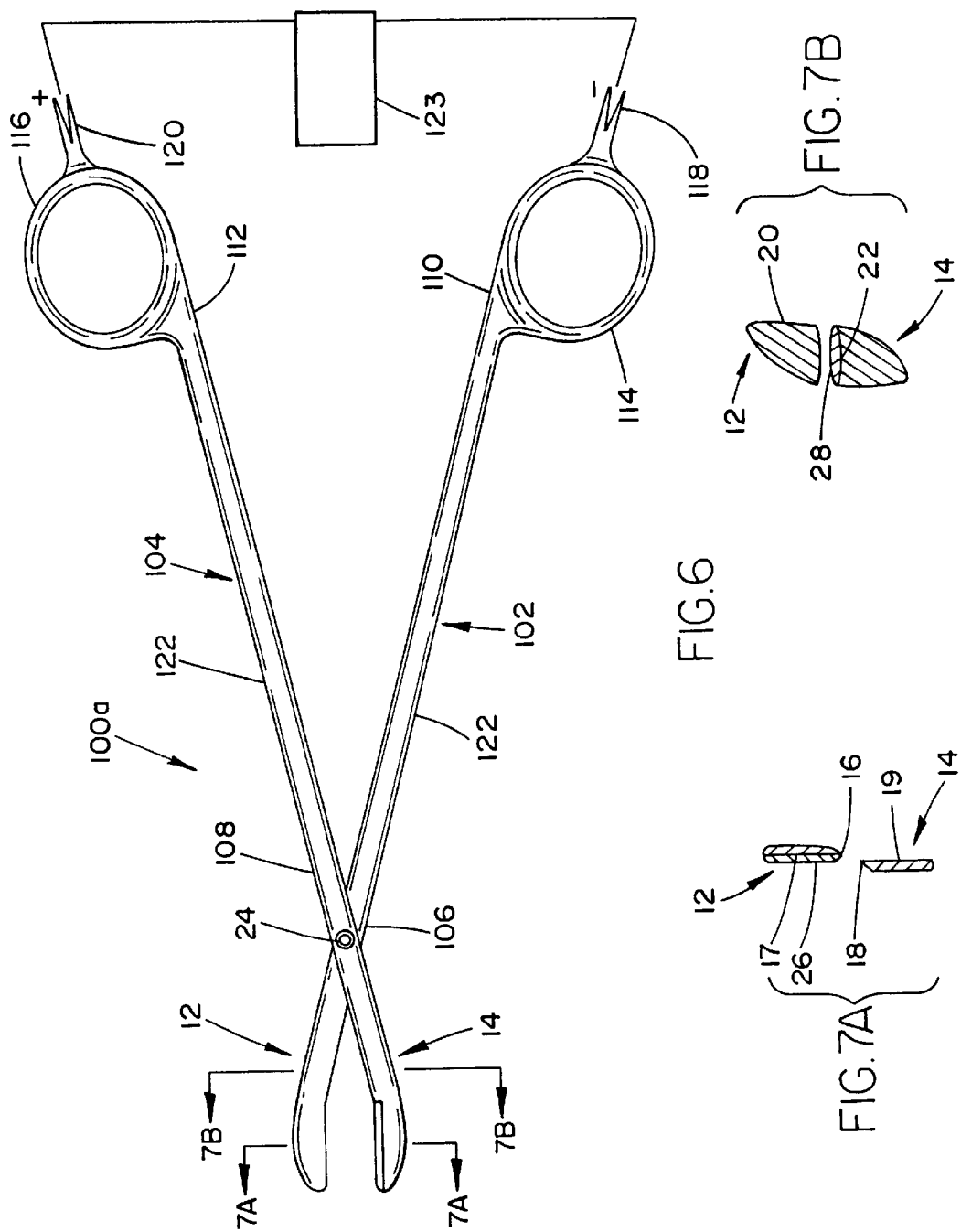

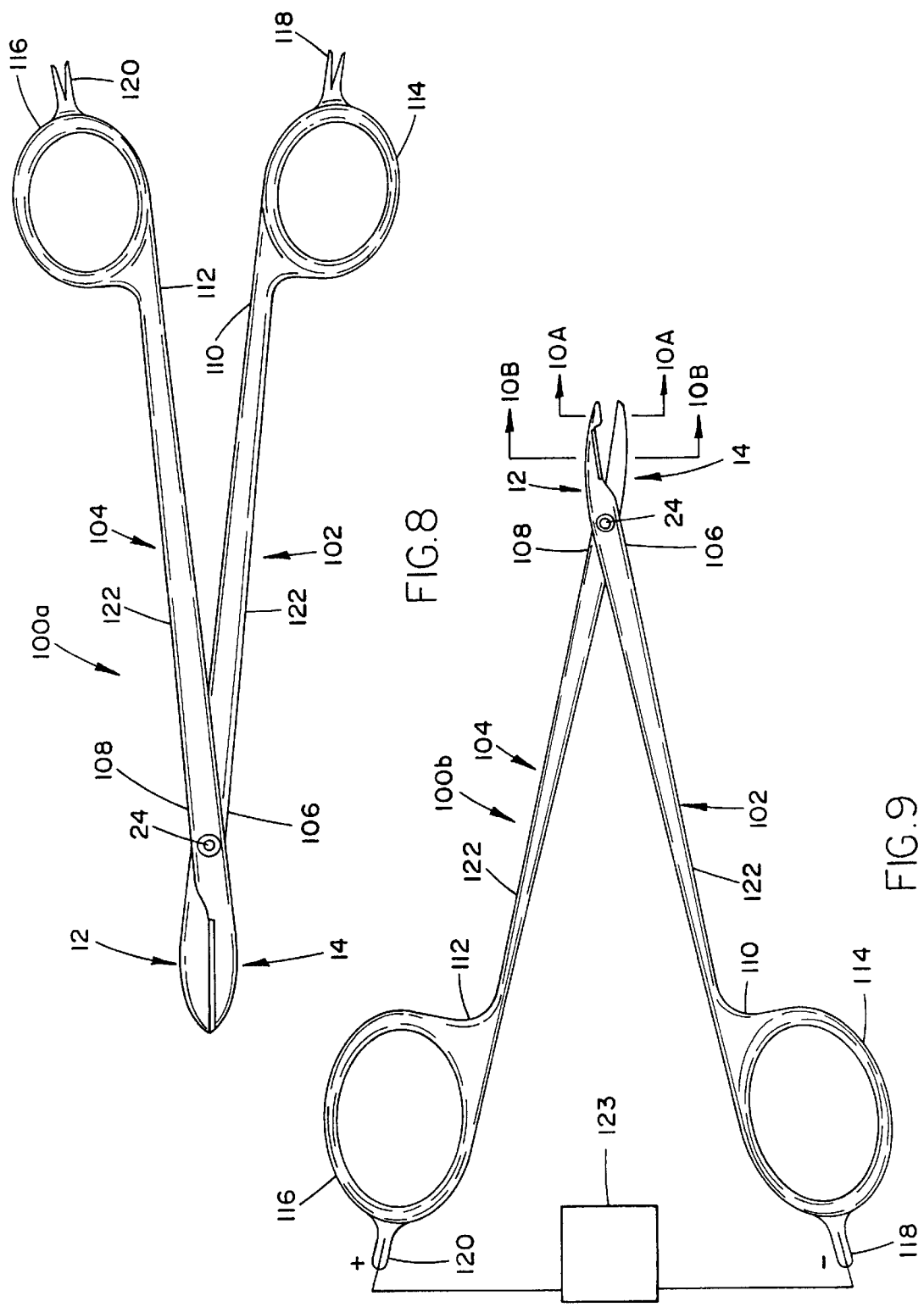

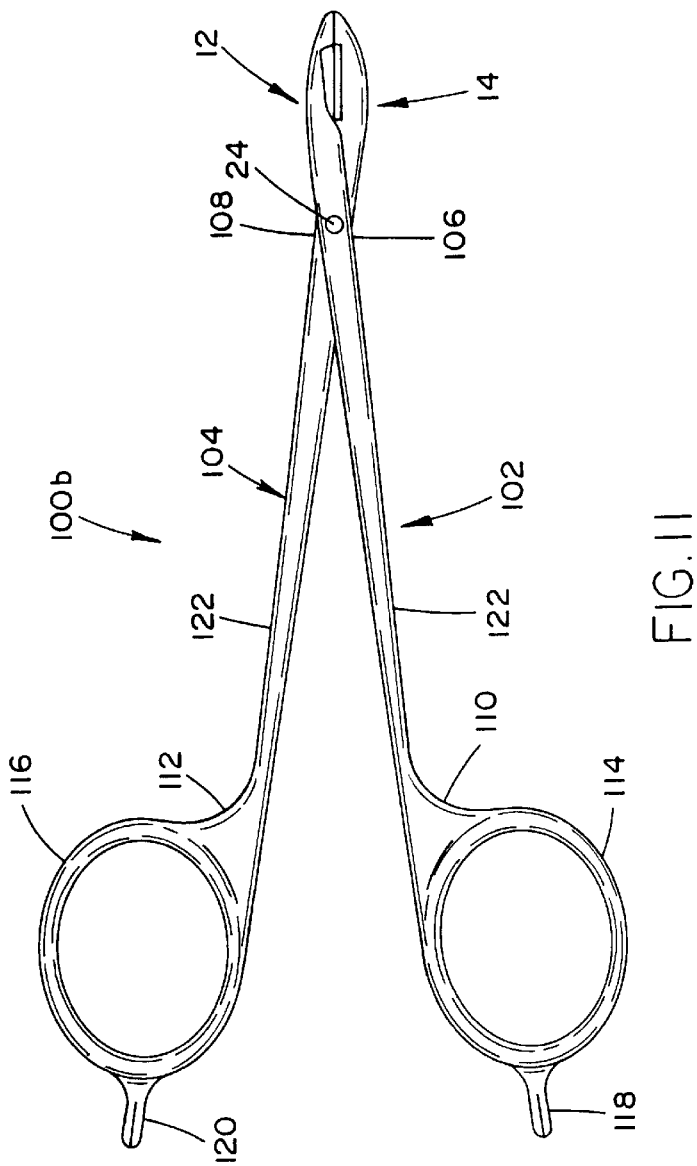

COMBINED BIPOLAR SCISSOR AND GRASPER

BACKGROUND OF THE INVENTION

1. Field of the Invention

The field of art to which this invention relates is surgical instruments, in particular, electrosurgical cutting and grasping instruments.

2. Description of the Related Art

Surgery requires the use of surgical instruments within a restricted and unusually sensitive operating field. During surgery, the field becomes crowded if a large number of surgical instruments must be used simultaneously, with concomitant difficulty for the surgical team to maintain a clear viewing area. Under such circumstances, surgical instruments designed to perform more than one task are of particular importance.

Two techniques used extensively in both open and endoscopic surgery are (a) the controlling of bleeding using electrosurgical instrumentation and (b) the incision or severing of tissue or vessels. The control of bleeding during surgery accounts for a major portion of the time involved in surgery. In particular, bleeding that occurs when tissue is incised or severed can obscure the surgeon's vision, prolong the operation, and adversely effect the precision of cutting. Blood loss from surgical cutting may require blood infusion, thereby increasing the risk of harm to the patient.

Hemostatic electrosurgical techniques are known in the art for reducing bleeding from incised tissue prior to, during, and subsequent to incision. Electrosurgical cutting and coagulating instruments are used to perform such techniques. These instruments can be of a reusable type (which require cleaning and disinfecting or sterilizing before each use) or disposable (which are disposed of after a single use). Each type includes both monopolar and bipolar variations having at least one electrode. Radio frequency (RF) energy is conducted through this electrode to either a remote conductive body-plate (known as a grounding pad) in the case of monopolar instruments, or to a second, closely spaced conductive electrode in the case of bipolar instruments. In monopolar instruments electrical current travels from the electrode through the patient's body to the grounding pad. Bipolar instruments are typically connected to both poles of an electrosurgical generator, therefore current flow is typically limited to tissue adjacent to the working end of the bipolar instrument (where the two electrodes are located).

Prior to the advent of electrosurgical cutting instruments, a surgeon would perform any cutting with a scissors and coagulate with an entirely different instrument. This exchange of instrumentation was time consuming. In response for the need to have a scissors-type instrument for cutting but which also incorporated the ability to coagulate blood and other body tissue using RF energy, electrosurgical cutting devices have been developed which combine mechanical cutting with electrosurgical cauterization, coagulation, and cutting.

Standard shape and size scissors have evolved in the surgical arts which surgeons have become accustomed to. These standards have been incorporated into the electrosurgical cutting instruments, not only because they have been tested by time and found to be very functional, but mainly because surgeons have become accustomed with their feel and use. Examples of some of these standards include the Mayo, Metzenbaum, and Tenotomy scissors. Each standard scissor is typically available in both curved and straight variations.

Grasper or forcep type instruments are also well known in the art. They generally consist of opposing jaws which pivot about a pivot point into an open or closed position. In a closed position the jaws of the grasper provide a means to grasp and hold, or grasp and tear, a piece of body organ, a vessel, or tissue.

Electrosurgical graspers have been developed to cauterize a portion of tissue. This is accomplished in one of two ways. Cauterization can be accomplished by using an outside surface or the tip of both jaws to cauterize the tissue the jaws contact. Cauterization can also be accomplished with a grasper by grasping down onto tissue and cauterizing the tissue between the jaws. It is in this way that electrosurgical graspers are used to coapt a vessel prior to transection with a cutting device. Electrosurgical graspers are also used to coapt retracted bleeders (severed blood vessels).

In practice, vessels are coapted in several ways. One such way is by using a standard grasper not capable of cauterization and a monopolar pencil. The vessel is first clamped between the jaws of the grasper, and the pencil is used to energize the grasper with RF energy. The RF energy passes from the monopolar pencil, through the forceps, vessel and patients body to the grounding pad. This is a potentially dangerous procedure. The patient or surgeon can be easily injured in such a procedure.

Another way to perform coaptation of vessels is by using a monopolar or bipolar scissors in which the scissors are rotated exposing the vessel to the side surfaces of the scissor's blades. In theory, the blade sides cauterize the vessel and the vessel is then severed with the scissors. In practice, this procedure is very difficult and can lead to complications. It is very easy for a surgeon to nick the vessel with the scissor blades before the coaptation of the vessel is complete, causing unanticipated bleeding and the need for further instrumentation to stop the bleeding.

Whichever method of coaptation is used, subsequent to the coaptation, the vessel is severed by a cutting instrument such as an electrosurgical scissor. In light of the above discussion, this procedure has been most effectively and safely accomplished with at least two different surgical instruments, a grasper to grasp and coapt, and a scissor to sever the coapted vessel.

Tidemand, U.S. Pat. No. 5,342,381, discloses an endoscopic combination bipolar scissors and forceps instrument which has blade and forceps portions on each of two jaws. Although the Tidemand instrument is useful it is subject to several disadvantages which effect the performance of the device, especially with regard to coaptation of vessels.

Since the blades of the Tidemand invention are insulated (typically ceramic) the blades themselves only offer mechanical cutting. As discussed previously, an instrument which offers both mechanical and electrosurgical cutting is preferred over one which offers only the former. Additionally, certain procedures require that the scissors portion of the instrument be distal to the graspers. Likewise, some procedures require the grasper portion of the instrument to be distal to the scissor portion. Tidemand discloses only the latter configuration, which is inadequate in many surgical procedures.

Furthermore, the shape and size of the cutting and grasping surfaces in the Tidemand instrument are awkward, unlike any standard scissor that surgeons have become accustomed to.

With regard to surgical procedures in which coaptation of vessels is required, the Tidemand combination instrument could not be effectively utilized. Effective coaptation requires hemostasis during cutting as well as during grasping (or clamping) in order to cauterize the ends of the severed vessel.

Like the Tidemand instrument, the single feature electrosurgical cutting devices and graspers of the prior art are useful and effective, but they too suffer from several deficiencies associated with their use. The instrument exchange associated with cutting, coagulating and coaptation requires dexterity on the part of the surgeon. The increased number of instruments has the disadvantage of crowding the operating field. Additionally, their is a greater burden on assistant personnel in the operating room, such as nurses, because of the exchange of instrumentation between them and the surgeon.

Another disadvantage of the prior art concerns cleaning, disinfecting and sterilization (CDS) issues known in the surgical instrumentation art. Transmission of sickness and disease through contaminated instrumentation is a very real problem in the medical field. Typically, surgical instrumentation is cleaned and disinfected or sterilized after each use to minimize this possibility. Since effective coaptation of vessels has required two instruments, a graspers and a scissors, the risk of disease transmission is increased. The explanation for this is purely statistical, the probability of transmitting disease in two instruments is greater than for a single instrument.

Additionally, the cost of processing (cleaning, disinfecting or sterilizing) two reusable instruments and purchasing two reusable instruments is greater than the costs associated with a single combined instrument.

To combat the CDS problems associated with reusable instruments, disposable instruments have been developed which are disposed after a single use. While they have their advantages, disposable instruments suffer from the disadvantage of contributing to the amount of medical waste generated.

The prior art disposable scissors and graspers suffer the disadvantage of contributing twice the medical waste as a single disposable instrument combining both features. Likewise, the cost of two disposable surgical instruments is greater than the cost of a combined disposable instrument.

Accordingly, there is a need in the art for an improved electrosurgical instrument having mechanical grasping and cauterization capabilities to coapt vessels combined with capabilities to mechanically transect and cauterize the vessel, contained within a standard scissors shape and size.

SUMMARY OF THE INVENTION

Therefore, it is an object of the present invention to provide a single bipolar electrosurgical instrument which is capable of performing the functions of both a bipolar forceps and a bipolar scissors.

It is yet a further object of the present invention to provide a bipolar surgical instrument which combines a bipolar scissors and bipolar grasper with the grasping portions contained within a standard scissor shape and size.

It is yet a further object of the present invention to provide a bipolar surgical instrument to eliminate the need to energize a standard grasper with a monopolar pencil.

It is yet a further object of the present invention to provide a bipolar surgical instrument to eliminate the need to rotate a monopolar or bipolar scissors to coapt a vessel.

It is yet another object of the present invention to provide a combined bipolar cutting and grasping instrument which provides for improved cauterization and coagulation.

It is yet another object of the present invention to provide a combined bipolar cutting and grasping instrument which reduces the amount of instrumentation necessary for surgical procedures in which both electrosurgical cutting and grasping is required.

It is yet another object of the present invention to provide a combined bipolar cutting and grasping instrument which reduces the burden on assistant personnel in an operating room in which a surgical procedure is being performed that requires both electrosurgical cutting and grasping.

It is yet another object of the present invention to provide a combined bipolar cutting and grasping instrument which reduces the amount of dexterity needed by a surgeon performing a surgical procedure in which both electrosurgical cutting and grasping is required.

It is yet another object of the present invention to provide a combined bipolar cutting and grasping instrument which reduces the costs associated with surgical procedures in which both electrosurgical cutting and grasping is required.

It is yet another object of the present invention to provide a combined bipolar cutting and grasping instrument which decreases the probability of transmission of disease due to contaminated instrumentation in surgical procedures in which both electrosurgical cutting and grasping is required.

It is still yet another object of the present invention to provide a combined disposable bipolar cutting and grasping instrument which decreases the amount of medical waste generated in surgical procedures in which both electrosurgical cutting and grasping is required.

Accordingly, a combined bipolar electrosurgical cutting and grasping instrument is disclosed. The device has a first jaw member. The first jaw member further having a first cutting edge, a first cutting surface, a portion of its length as a first grasping surface, and a first pivoting surface. A second jaw member has a second cutting edge, a second cutting surface, a second grasping surface, and a second pivoting surface. The cutting edges and the grasping surfaces oppose each other. Furthermore, the pivoting surfaces oppose each other and are in sliding contact with each other. The first and second jaw members are pivotally connected by a pivot pin where at least one of the jaw members pivots relative to the other such that when pivoted from an open position to a closed position the grasping surfaces come into substantial contact and the cutting edges engage in a shearing motion. A means for supplying electrical energy to the first jaw member and electrical energy of the opposite polarity to the second jaw member is provided. An isolating means for electrically isolating the first jaw member from the second jaw member is also provided. Lastly, an actuation means is provided for opening and closing the jaw members between their open and closed positions.

In another embodiment of the present invention, the cutting edges are distal to the grasping surfaces.

In yet another embodiment of the present invention, the grasping surfaces are distal to the cutting edges.

In a version of any of the above embodiments the grasping surfaces are contained within the shape and size of standard scissor blades.

In yet another version of any of the above embodiments, both jaw members pivot relative to each other.

In yet another version of any of the above embodiments the isolating means comprises electrically insulating coatings disposed on the first cutting surface, second cutting surface, and one of the first or second pivoting surfaces. Further provided is a means for preventing electrical conduction from the first jaw member to the second jaw member through the pivot pin.

In yet another version of any of the above embodiments, suitable for open surgical procedures, the present invention comprises first and second conductive elongated members as the means for actuation of the jaw members. Each elongated member having a distal and proximal end. Their distal ends respectively connected to the first and second jaw members. Each elongated member further having a finger loop portion at its proximal end for insertion of the user's fingers. The means for supplying electrical energy is provided by a first electrical connector disposed at the proximal end of the first elongated member and a second electrical connector disposed at the proximal end of the second elongated member. The instrument further comprising an insulating means for preventing electrical conduction from portions of the instrument other than those intended.

In yet another version of any of the above embodiments, suitable for endoscopic procedures, the present invention further having an elongated tube, having a distal end, a proximal end, and a lumen extending its entire width. The jaw members being pivotally disposed on the distal end of the tube. Also provided is an actuating means disposed on the proximal end of the tube for remote operation of the jaw members. The actuating means being of any type known in the art, such as a pistol grip or scissor type handles. The instrument further comprising an insulating means for preventing electrical conduction from portions of the instrument other than those intended.

Another aspect of the present invention are methods of using the various embodiments of the present invention for both open and endoscopic procedures.

BRIEF DESCRIPTION OF THE DRAWINGS

These and other features, and advantages of the instruments and methods of the present invention will become better understood with regard to the following description, appended claims, and accompanying drawings where:

FIG. 6 illustrates the instrument of FIG. 1A with the jaw members of the instrument being shown in the open position;

FIGS. 7A and 7B illustrate sectional views taken along lines 7A—7A and 7B—7B respectively in FIG. 6;

FIG. 8 illustrates the instrument of FIG. 1A with the jaw members of the instrument being shown in the closed position;

FIG. 9 illustrates the instrument of FIG. 2A with the jaw members of the instrument being shown in the open position;

FIGS. 10A and 10B illustrate sectional views taken along lines 10A—10A and 10B—10B respectively in FIG. 9;

FIG. 11 illustrates the instrument of FIG. 2A with the jaw members of the instrument being shown in the closed position;

DETAILED DESCRIPTION OF THE PREFERRED EMBODIMENTS

Figure 1A:
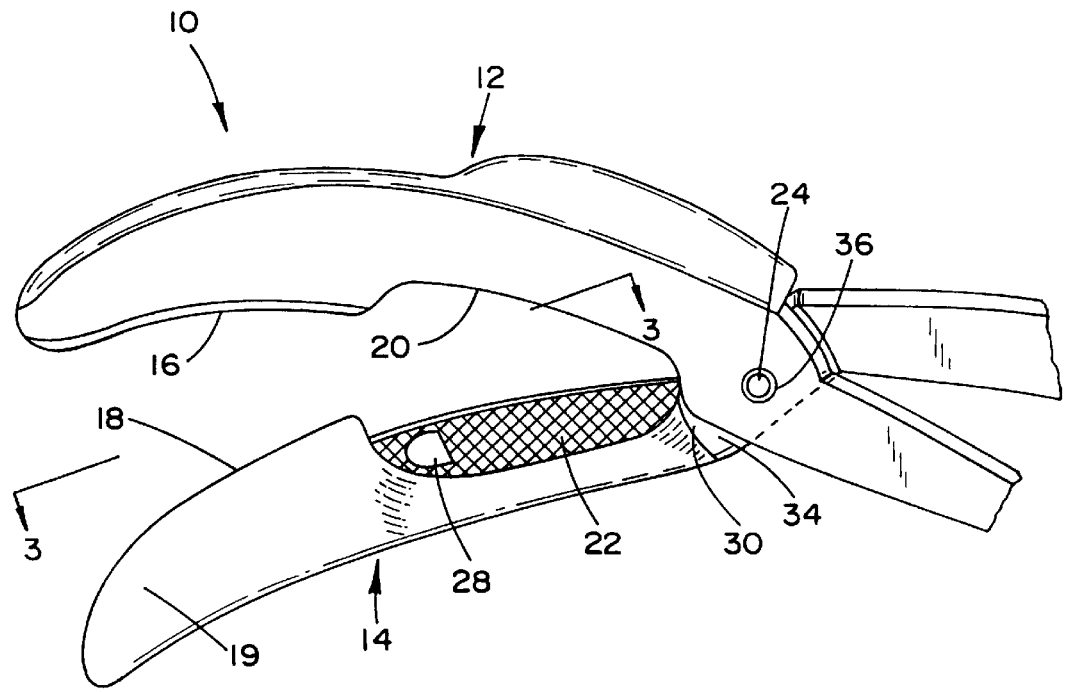
FIG. 1A illustrates an isometric view of the operating end of an embodiment of the present invention in which the scissors portion is distal, the jaw members thereof being shown in an opened position.
Figure 1B:
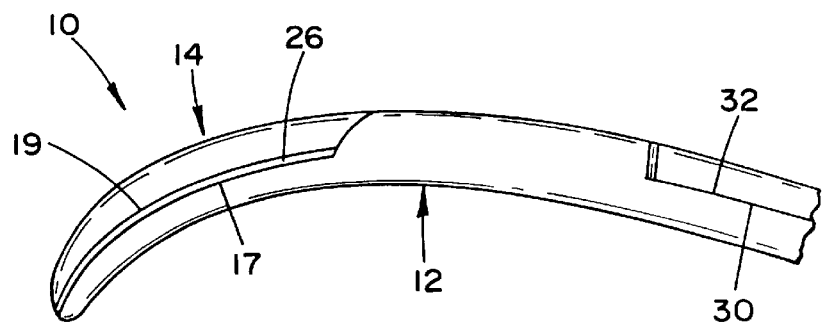
FIG. 1B illustrates the top view of the embodiment illustrated in FIG. 1A, the jaw members thereof being shown in a closed position.

Referring now in detail to FIGS. 1A and 1B there is illustrated the operating (or distal) end of the inventive combined bipolar scissors and grasper instrument 10 which includes first and second jaw members 12,14. Each jaw member having a cutting edge 16,18, a cutting surface 17,19, and a grasping surface 20,22. The cutting edges 16,18 and grasping surfaces 20,22 generally being constructed of a conductive material, preferably stainless steel. The first cutting edge 16 opposes the second cutting edge 18 and the first grasping surface 20 opposes the second grasping surface 22.

The first jaw member 12 further having a first pivoting surface 30. The second jaw member 14 further having a second pivoting surface 32. The pivoting surfaces 30,32 slidably contact each other at a point where the jaw members 12,14 intersect.

The jaw members 12,14 are pivotally connected by way of a rivet, screw, or pin 24 at their point of intersection such that they are capable of pivoting between an open and closed position. The point of intersection is configured with a conventional surgical scissors pivot.

Figure 1C:
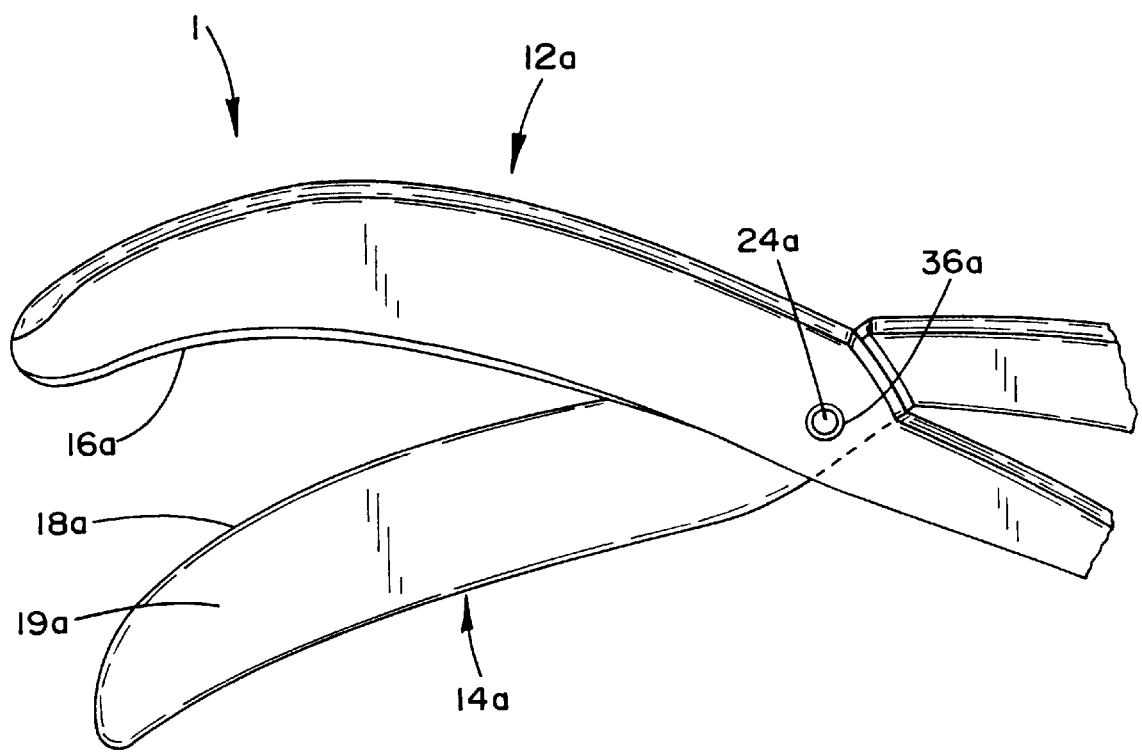
FIG. 1C illustrates an isometric view of the operating end of a typical bipolar surgical scissors of the prior art, the blade members thereof being shown in an opened position.
Figure 1D:
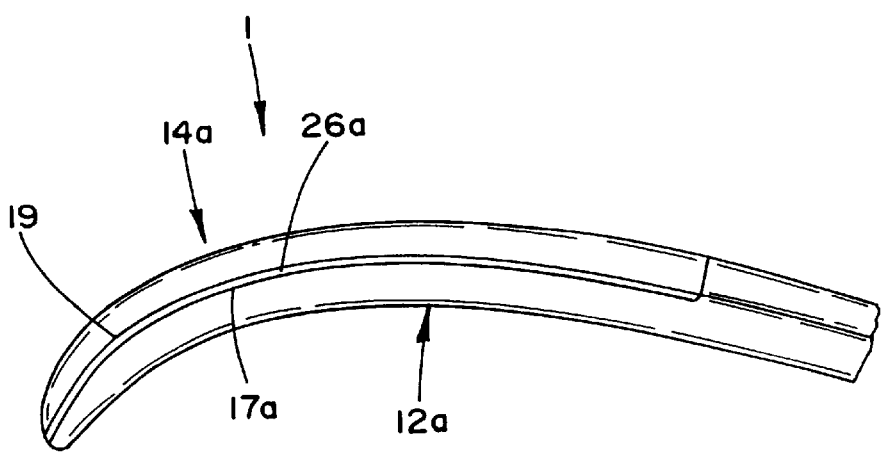
FIG. 1D illustrates the top view of the embodiment illustrated in FIG. 1C, the blade members thereof being shown in a closed position.

As shown in FIGS. 1C and 1D, a conventional bipolar surgical scissor is shown and referred to generally as reference numeral 1, wherein a first blade member 12a pivots about a second blade member 14a whereby they are retained into a pivoting relationship by a rivet, pin or screw 24a. Each blade member has a cutting edge 16a,18a and a cutting surface 17a,19a. A first electrically insulating coating 26a is applied to the first cutting surface 17a and a second insulating coating 36a is applied to the pin 24a for electrically isolating the first blade member 12a from the second blade member 14a. Therefore, electrical conduction is prevented from the first jaw member 12a to the second jaw member 14a through the rivet, pin or screw 24a.

Referring back to FIGS. 1A and 1B, when in the closed position, the first cutting edge 16 engages the second cutting edge 18 in a shearing motion. Similarly, the first grasping surface 20 substantially meets the second grasping surface 22 to form a clamp for grasping and clamping tissue or vessels therewithin.

Electrically insulating material is provided to electrically isolate the first jaw member 12 from the second jaw member 14. A first electrically insulating coating 26 is secured to the first cutting surface 17 thereby insulating the first cutting surface 17 from the second cutting surface 19 when the jaw members 12,14 are in their closed position but which allows electrical conduction between the first and second cutting edges 16,18 when tissue is present between the cutting edges 16,18.

Furthermore, a second insulating coating 28 is secured to the second grasping surface 22 thereby insulating the first grasping surface 20 from the second grasping surface 22. A third insulating coating 34 is supplied at the first pivoting surface 30. Lastly, a fourth insulating coating 36 is provided on the rivet, pin, or screw 24, to prevent electrical conduction from the first jaw member 12 to the second jaw member 14 through the pivot rivet, screw, or pin 24.

The insulating coatings 26, 28, and 34 are preferably aluminum oxide, plasma deposited on the instrument surfaces. The thickness of the aluminum oxide coatings can be between 0.003 and 0.010 inches thick, preferably between 0.005 and 0.007 inches thick to withstand a voltage of approximately 1,500 volts.

Preferably, the pivot pin, screw, or rivet 24 is similarly coated, but also can be fabricated from a high strength polymer, a glass-filled polymer, a ceramic-filled polymer, or fabricated entirely from a ceramic. If fabricated from a ceramic, it can be further impregnated with a polymer, such as PTFE, to improve its lubricity. Additionally, the pin, screw or rivet is typically epoxied in place with any suitable medical grade epoxy.

As shown in FIGS. 3A through 3D, the second insulating coating 28 preferably covers only a portion of the second grasping surface 22. When tissue is grasped between the first grasping surface 20 and second grasping surface 22, RF energy from one jaw member will be conducted to the other in the portions of the second grasping surface 22 which are uncoated, thereby cauterizing the tissue between the grasping surfaces 20,22 in the region of the uncoated portions.

Figure 3A:
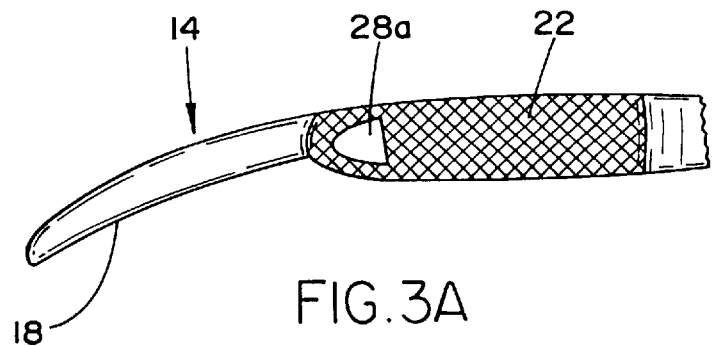
FIG. 3A illustrates a plan view of the second jaw member of the present invention as viewed along line 3—3 in FIG. 1A.
Figure 3B:
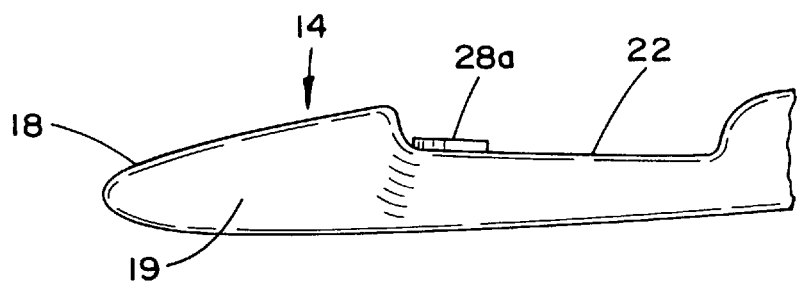
FIG. 3B illustrates a side view of the second jaw member of the present invention as illustrated in FIG. 3A.

Since the second insulating coating 28 covers only a portion of the second grasping surface 22 it can therefore take on a variety of shapes and sizes. FIG. 3A shows the second insulating coating 28a applied as a semi-circle across the width of the second grasping surface 22. The second insulating coating 28a is preferably raised above the second grasping surface 22, as shown in FIG. 3B, such that an insulating gap is maintained between the first grasping surface 20 and the second grasping surface 22 when the jaw members 12,14 are in their closed position. The insulating gap prevents electricity from being conducted from the first grasping surface 20 to the second grasping surface 22 when the jaw members 12,14 are in their closed position and tissue is not present between them.

It should be noted that the second insulating coating 28 is used to maintain an insulating gap between the first grasping surface 20 and the second grasping surface 22 equal to the thickness of the coating 28. The second insulating coating 28 can be eliminated and an insulating air gap used to isolate the first grasping surface 20 from the second grasping surface 22.

It should also be noted that the second insulating coating 28, as well as the first insulating coating 26, are not essential to the functioning of the instrument. They are provided for safety reasons to eliminate the possibility of electrical shorting between the jaw members 12,14 in the situation where the instrument is accidentally energized with RF energy while the jaw members 12,14 are in their closed position and tissue is not present between them. Such a situation where electrical shorting occurs between the jaw members 12,14 can be potentially dangerous to both the surgeon and patient.

Figure 3C:
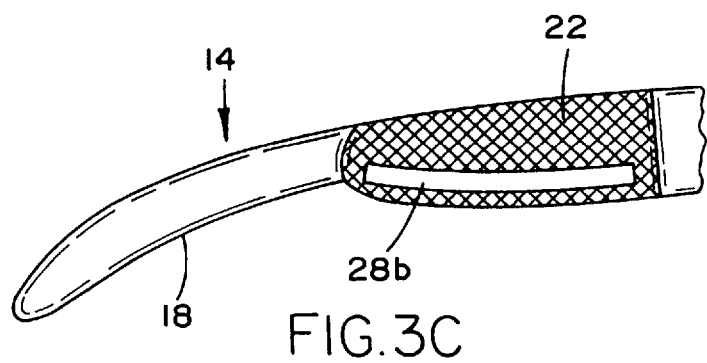
FIG. 3C illustrates a plan view of the second jaw member of an alternative version of the present invention as it would be viewed along line 3—3 in FIG. 1A.
Figure 3D:
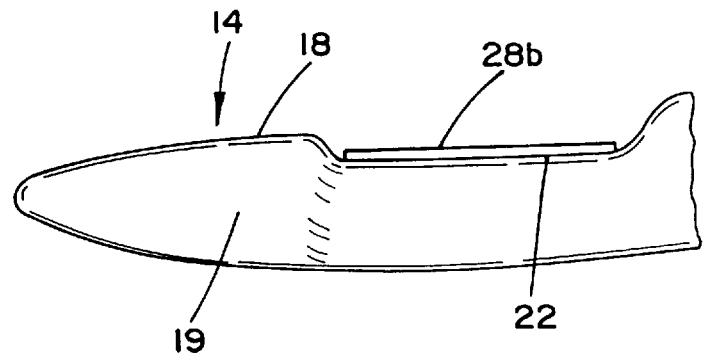
FIG. 3D illustrates a side view of the second jaw member of an alternative version of the present invention as illustrated in FIG. 3C.
Figure 4A:
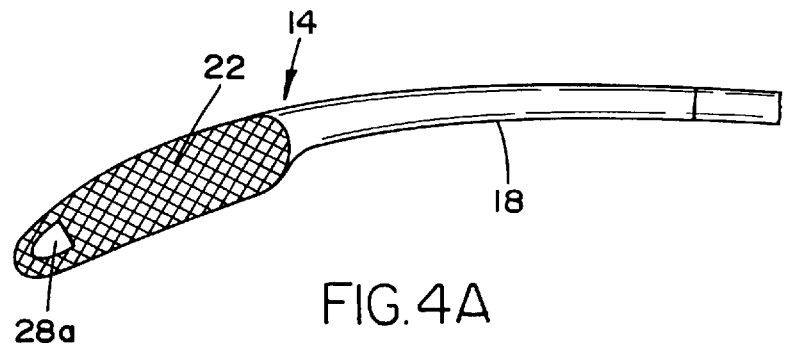
FIG. 4A illustrates a plan view of the second jaw member of the present invention as viewed along line 4—4 in FIG. 2A.
Figure 4B:
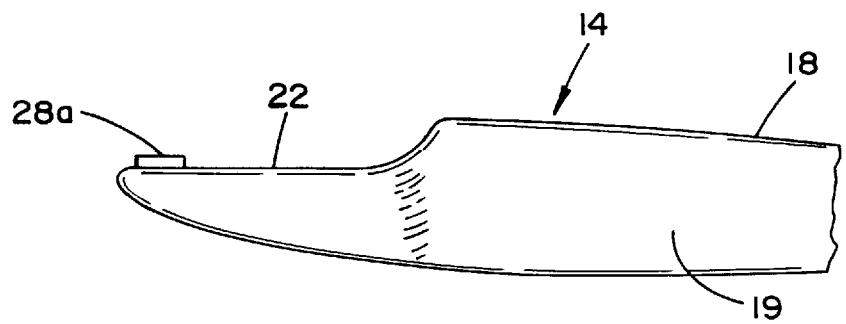
FIG. 4B illustrates a side view of the second jaw member of the present invention as illustrated in FIG. 4A.
Figure 4C:
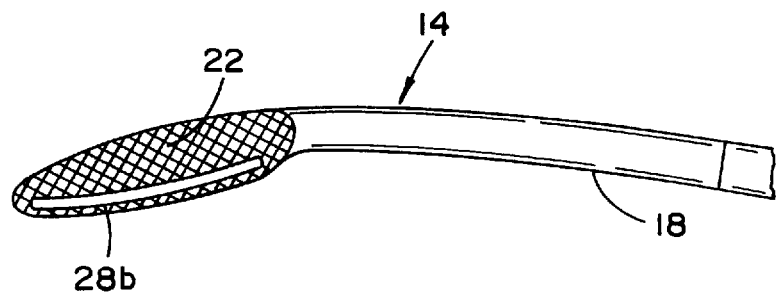
FIG. 4C illustrates a plan view of the second jaw member of an alternative version of the present invention as it would be viewed along line 4—4 in FIG. 2A.
Figure 4D:
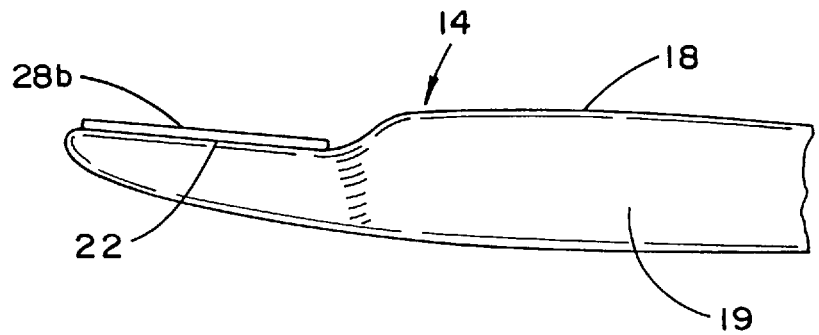
FIG. 4D illustrates a side view of the second jaw member of an alternative version of the present invention as illustrated in FIG. 4C.

Similarly, FIG. 3C shows an alternatively shaped second insulating coating 28b applied as a strip across the length of the first grasping surface 20. FIG. 3D shows that the second insulating coating 28b is likewise raised above the second grasping surface 22 such that an insulating gap is maintained between the first grasping surface 20 and the second grasping surface 22 when the jaw members 12, 14 are in their closed position.

Referring back to FIGS. 1A and 1C, as shown clearly in a comparison of FIGS. 1B and 1D, the shape of the instrument's distal end does not vary from the shape of a standard scissor's blades 12a,14a even though grasping surfaces 20,22 have been incorporated therein. Since the grasping surfaces 20,22 follow the contours of a standard scissor shape, the feel and use of the standard scissor is maintained for the combined instrument.

Figure 2A:
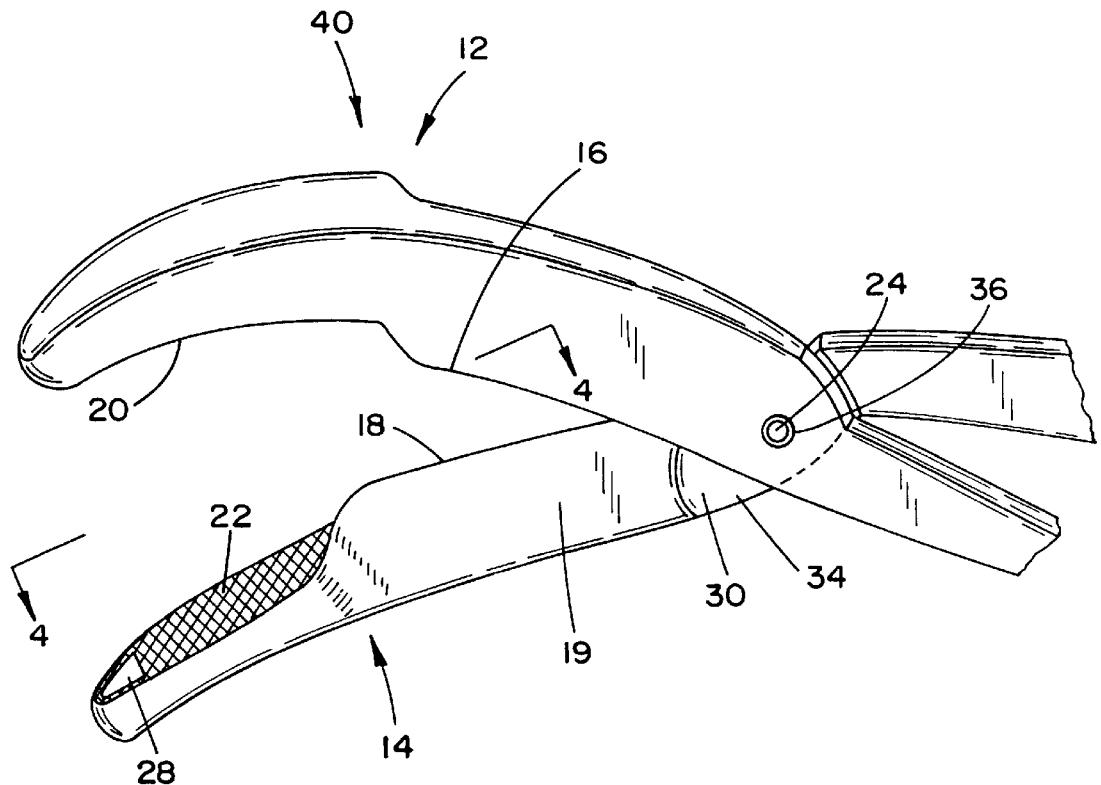
FIG. 2A illustrates an isometric view of the operating end of an embodiment of the present invention in which the graspers portion is distal, the jaw members thereof being shown in an opened position.
Figure 2B:
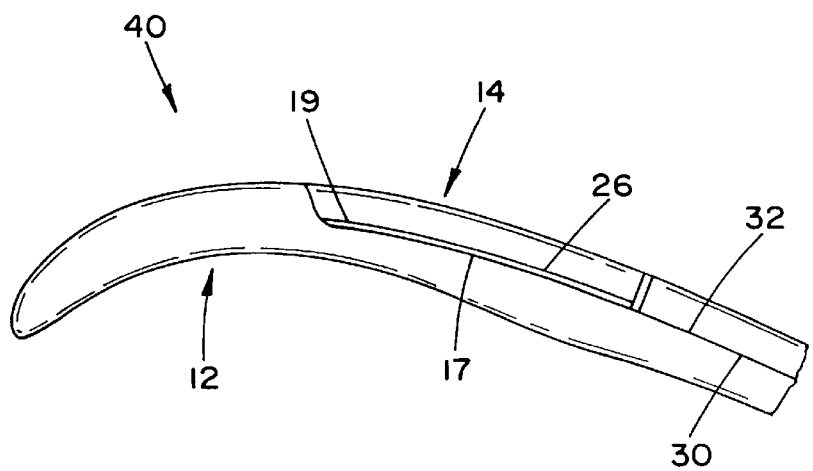
FIG. 2B illustrates the top view of the embodiment illustrated in FIG. 2A, the jaw members thereof being shown in a closed position.

FIGS. 1A and 1B illustrate an embodiment of the present invention 10 configured to have the cutting edges 16,18 distal to the grasping surfaces 20,22. FIGS. 2A and 2B illustrate a similar embodiment of the present invention 40 in which all components similar to or identical with those in FIGS. 1A and 1B are designated by the same reference numerals, and is merely modified with regard to the previous embodiment, in that the jaw members 12,14 are configured to have the grasping surfaces 20,22 distal to the cutting edges 16,18. Similarly, FIGS. 4A through 4D illustrate two variations of the second insulating surface 28a,28b similar to those previously discussed and shown in FIGS. 3A through 3D.

As shown clearly in FIG. 2B, the shape of the instrument's distal end does not vary from the shape of a standard scissor, even though grasping surfaces 20,22 have been incorporated therein. Since the grasping surfaces 20,22 follow the contours of a standard scissor shape, the feel and use of the standard scissor is maintained for the combined instrument. Since the width of the scissor tapers down toward the distal tip, less grasping surface is available in this configuration than in the configuration shown in FIGS. 1A and 1B. However, each configuration is useful and more effective in certain surgical procedures depending upon the cutting and grasping requirements for the procedure.

Figure 5A:
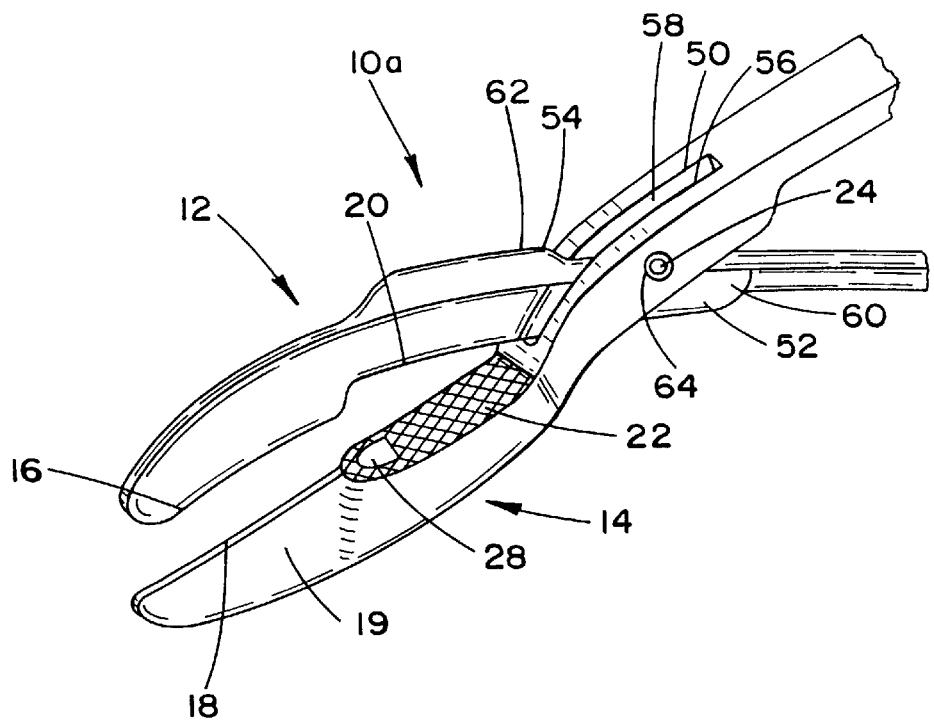
FIG. 5A illustrates a box-lock version of the present invention as shown in FIG. 1A.
Figure 5B:
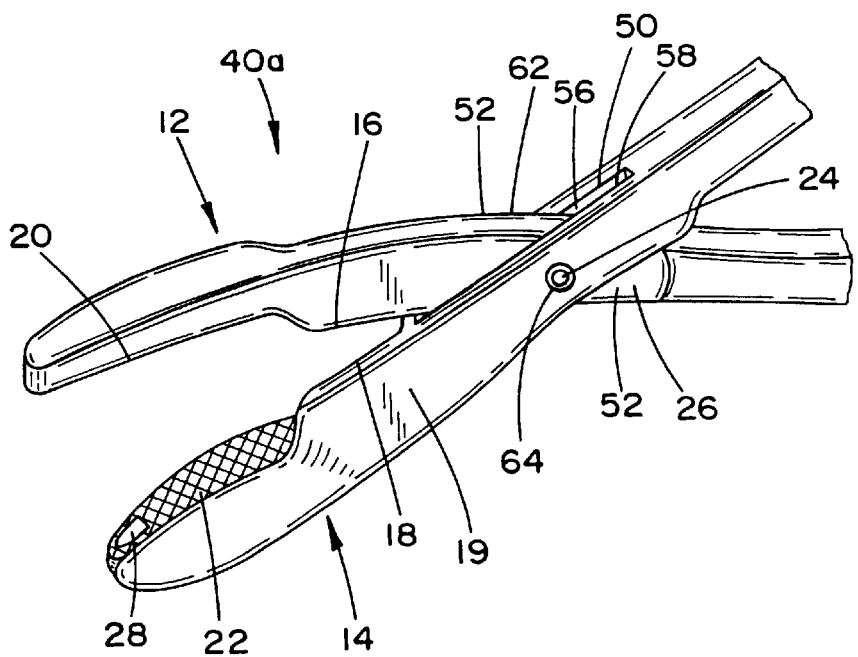
FIG. 5B illustrates a box-lock version of the present invention as shown in FIG. 2A.

Referring now to FIGS. 5A and 5B there is illustrated the embodiments of FIGS. 1A and 2A, respectively, in which the standard scissor pivot configuration is replaced by a box-lock pivot configuration. FIG. 5A illustrates an instrument 10a of the present invention configured with the scissors portion distal to the grasping portion. In the box-lock configuration shown, the first jaw member 12 is retained within, and pivots within a slot 50 disposed in the second jaw member 14. In addition, the first member 12 has a first and second pivoting surface 52,54 and the second member 14 has a third and fourth pivoting surface 56,58. The first pivoting surface 52 being in sliding contact with the third pivoting surface 56 and the second pivoting surface 54 being in sliding contact with the fourth pivoting surface 58. Third and fourth insulating coatings 60,62 are needed on the first and second pivoting surfaces 52,54 on the first jaw member 12 in order to isolate the first jaw member 12 from the second jaw member 14. A fifth insulating coating 64 is disposed around the pin, rivet, or screw 24 to complete the electrical isolation of the first jaw member 12 from the second jaw member 14. Otherwise, all components are similar to, or identical with, those in FIG. 1A and are designated with the same reference numerals.

Referring now to FIG. 5B, there is illustrated an instrument of the present invention configured with the graspers portion distal to the scissors portion, similar to the instrument shown in FIG. 2A. The instrument illustrated in FIG. 5B differs in that it replaces the conventional scissor pivoting means with a box-lock pivot means. This embodiment is similar to the embodiment shown in FIG. 5A except for the grasper portion being distal to the scissor portion. In a variation of this configuration, the first insulating coating 26 can be extended to the first pivoting surface 52, thereby eliminating the need for a separate fourth insulating coating 60. Otherwise, all components are similar to, or identical with, those in FIG. 2A and are designated with the same reference numerals.

The embodiment as configured in FIGS. 1A and 1B with the scissors portion distal to the grasping portion is preferred for procedures that require cauterization of larger vessels, or groups of vessels. It is particularly suited for procedures requiring cauterization of vessels larger than three millimeter in diameter. The coagulation of ovarian vessels in an "Oophorectomy" is representative of such a procedure.

The embodiment as configured in FIGS. 2A and 2B with the graspers portion distal to the scissors portion is preferred for those procedures requiring extensive blunt dissection. Procedures requiring separation of connective tissue to free vein and artery, such as "Pericardiectomy for Constrictive Pericarditis" and "Harvesting for a Free Greater Omentum Transfer" are examples of such procedures.

Furthermore, there are procedures where either configuration could be used, and the surgeon would want a choice of either instrument.

Mayo, Metzenbaum, and Tenotomy standard shape scissors have been discussed in relation to the present invention. However, it should be understood that any standard shape scissor now known or later developed can be employed in the present invention. A point of novelty, among others, thereof being the inclusion of grasping surfaces in a standard scissor shape whereby the contours, shape, and size of the scissor is maintained, thus preserving the same feel and use as the standard scissor. It should also be understood that any standard scissor shape used in the present invention can be configured in either a straight blade or curved blade configuration.

Referring now to FIG. 6, the operating (or distal) end of the present invention as shown in FIGS. 1A and 1B is integral with an actuation means for opening and closing the jaw members 12,14 relative to each other resulting in an embodiment of the present invention 100a useful for open surgical procedures. The actuation means comprises first and second conductive elongated members 102,104. Each elongated member having a distal end 106,108 and a proximal end 110,112. The first jaw member 12 being integral with the distal end 106 of the first elongated member 102. The second jaw member 14 being disposed on the distal end 108 of the second elongated member 104.

The first elongated member 102 pivots about the second elongated member 104 about the pivot pin, screw or rivet 24. First and second finger loops 114,116 are provided at the proximal ends 110,112 of the elongated members 102,104 for insertion of fingers for actuation of the jaw members 12,14 between an open position as shown in FIG. 6 and a closed position as shown in FIG. 8.

Referring back to FIG. 6, a means for supplying RF energy to the first jaw member 12 and RF energy of the opposite polarity to the second jaw member 14 is accomplished by first and second conductive connectors 118,120 disposed at the proximal ends 110,112 of the elongated members 102,104 for connection to a power cord (not shown).

The power cord typically connects to an electrosurgical generator 123 which energizes each of the electrical connectors 118,120 with RF energy used to cauterize tissue. In a bipolar configuration, the first electrical connector 118 is supplied with RF energy having a certain polarity, while the second electrical connector 120 is supplied with RF energy of the opposite polarity.

Since the electrical connectors 118,120, the As elongated members 102,104, and the jaw members 12,14 are typically conductive, the RF energy is transported from the electrical connectors 118,120, through the elongated members 102, 104, to the jaw members 12,14. To protect and insulate a user from shock, the elongated members 102,104 along with the finger loops 114,116 are coated with an electrically insulating material 122, preferably nylon to prevent electrical conduction from portions of the instrument other than those intended. Typically, the insulating coating 122 extends just past the pivot pin, rivet, or screw 24 leaving only the electrical connectors 118,120 and most of the jaw members 12,14 exposed. Since the first jaw member 12 is electrically isolated from the second jaw member 14 the RF energy supplied at electrical connector 118 will not short with the opposite polarity RF energy supplied at electrical connector 120 unless tissue is present between the jaw members 12,14 to complete their circuit.

Referring now to FIGS. 7A and 7B, FIG. 7A is taken along the line 7A—7A in FIG. 6 illustrating a sectional view of cutting edges 16,18 and the insulated coating 26 secured to the first cutting edge 16. Similarly, FIG. 7B is taken along the line 7B—7B in FIG. 6 illustrating a sectional view of grasping surfaces 20,22 and the insulated coating 28 secured to the second grasping surface 22.

The embodiment shown in FIGS. 6, 7A, 7B, and 8 can also be configured in the box-lock configuration shown in FIG. 5A and in any standard scissor configuration now known or later developed in the surgical arts. Furthermore, any of these configurations can be of a reusable or disposable nature.

The embodiment illustrated in FIGS. 9, 10A, 10B, and 11, generally referred to by reference numeral 100b, in which all components similar to or identical with those in FIGS. 6, 7A, 7B, and 8 are designated with the same reference numerals, is merely modified with regard to the previous embodiment, in that the configuration of jaw members 12,14 is as shown in FIGS. 2A and 2B where the grasping surfaces 20,22 are distal to the cutting edges 16,18.

The embodiment shown in FIGS. 9, 10A, 10B, and 11 can also be configured in the box-lock configuration shown in FIG. 5B or in any standard scissor configuration now known or later developed in the surgical arts. Furthermore, any of these configurations can be of a reusable or disposable nature.

Figure 12A:
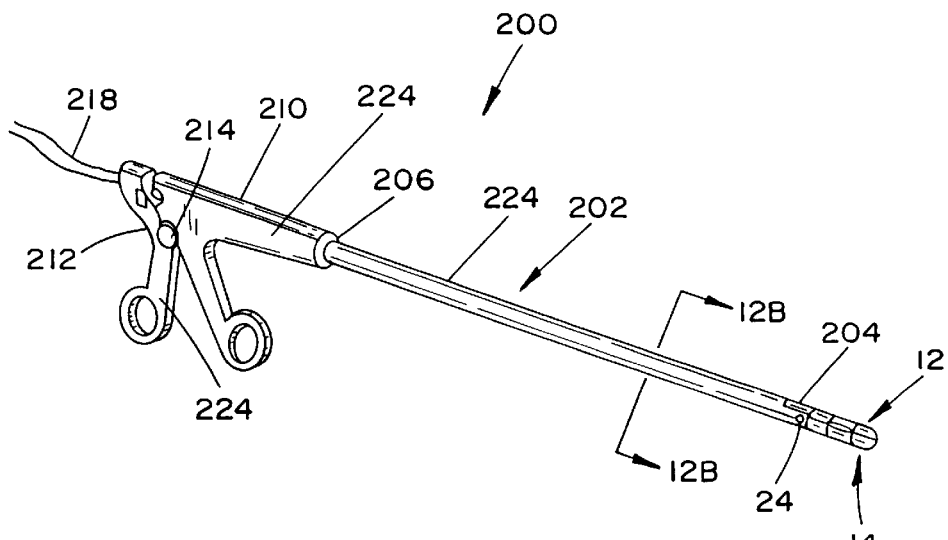
FIG. 12A illustrates an endoscopic embodiment of the present invention having a scissors grip.
Figure 12B:
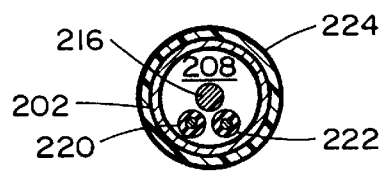
FIG. 12B illustrates a sectional view taken along the line 12B—12B in FIG. 12A.
Figure 13:
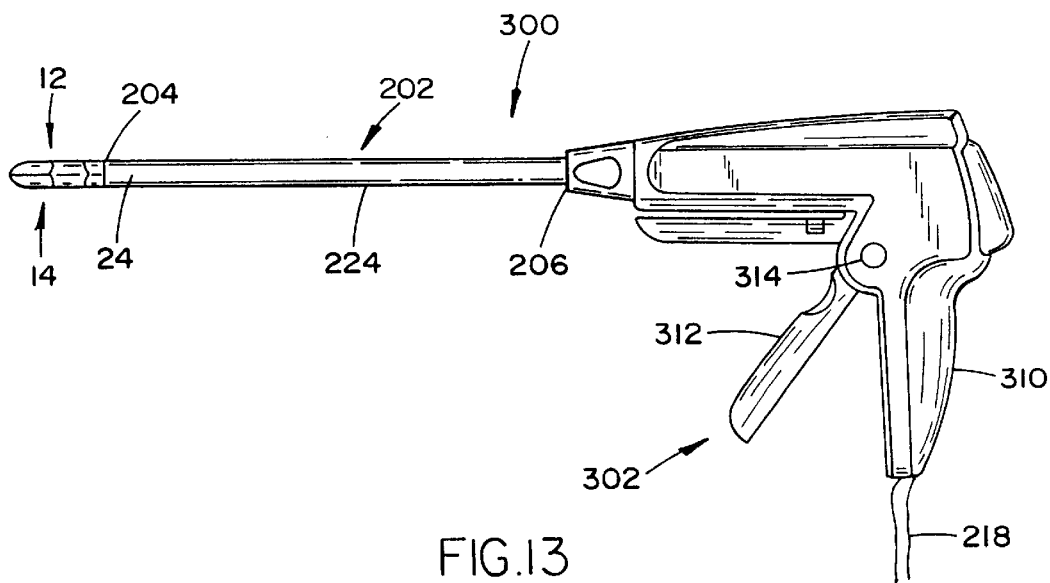
FIG. 13 illustrates an endoscopic embodiment of the present invention having a pistol grip.

FIGS. 12A, 12B, and 13 illustrate the present invention configured to be utilized in endoscopic surgical procedures. Referring to FIG. 12A, an endoscopic bipolar combination graspers/scissors instrument 200 is shown. The instrument having an elongated tube 202, the tube 202 having a distal end 204, a proximal end 206, and a central lumen 208. The first and second jaw members 12,14 are pivotally disposed on the distal end 204 of the elongated tube 202 such that they pivot about the pivot pin, rivet, or screw 24 which is also fixed to the distal end 204 of the elongated tube 202.

First and second handle members 210,212 are provided at the proximal end 206 of the elongated tube 202. The first handle member 210 being fixed to the proximal end 206 of the elongated tube 202 and the second handle member 212 being pivotally connected to the first handle member 210 about a pivot pin, rivet, or screw 214. The second handle member 212 is connected to the jaw members 12,14 by a wire member 216 disposed through the lumen 208 of the elongated member 202. The wire member 216 is connected at one of its ends to the second handle member 212 and at its other end to a suitable endoscopic actuating mechanism (not shown) for actuating the jaw members 12,14 such that pivoting of the second handle member 212 about the pivot pin, rivet, or screw 214 causes the jaw members 12,14 to open and close relative to each other. Suitable endoscopic actuating mechanisms are numerous in the surgical arts, any one of which can be employed in the endoscopic version 200 of the present invention.

RF energy is supplied to the jaw members 12,14 by a power cord 218 which is connected to an electrosurgical generator 123. The power cord contains two insulated leads 220,222 which are fed through the lumen 208 of the elongated tube 202. The first and second leads 220,222 are electrically connected respectively to the first and second jaw members 12,14 supplying the jaw members 12,14 with RF energy of different polarities. Since the first jaw member 12 is electrically isolated from the second jaw member 14 the RF energy supplied the first insulated lead 220 will not short with the opposite polarity RF energy supplied from the other insulated lead 222 unless tissue is present between the jaw members 12,14 to complete their circuit.

To protect the user from electrical shock, the handle members 210,212 and elongated tube 202 are either made of a non-conductive material, such as a suitable thermoplastic, or coated with a insulating material 224, such as nylon. In the case where the coating of insulating material 224 is used, the pin, rivet, or screw 214 is also coated with a insulating material to isolate the first handle member 210 from the second handle member 212 as well as to protect the user from electrical injury.

The embodiment illustrated in FIGS. 12A and 12B of the drawings in which all components similar to or identical with those in FIG. 13 are designated with the same reference numerals, is merely modified with regard to the previous embodiment, in that the bipolar endoscopic combination scissors/graspers 300 illustrated in FIG. 13 uses a pistol grip 302, actuating means having a first handle member 310, and a second handle member 312. The second handle member 312 is connected to a suitable endoscopic actuating mechanism known in the art (not shown) for actuation of the jaw members 12,14 when the second handle member 312 is pivoted about the pivot pin, rivet, or screw 314 causing the jaw members 12,14 to open and close.

The jaw members 12,14 of FIGS. 12A and 13 can be configured in any way illustrated in FIGS. 1A and 2A or in any standard scissor configuration now known or later developed in the surgical arts. Furthermore, the embodiments illustrated in FIGS. 12A and 13 can be of a reusable or disposable nature.

Figure 14:
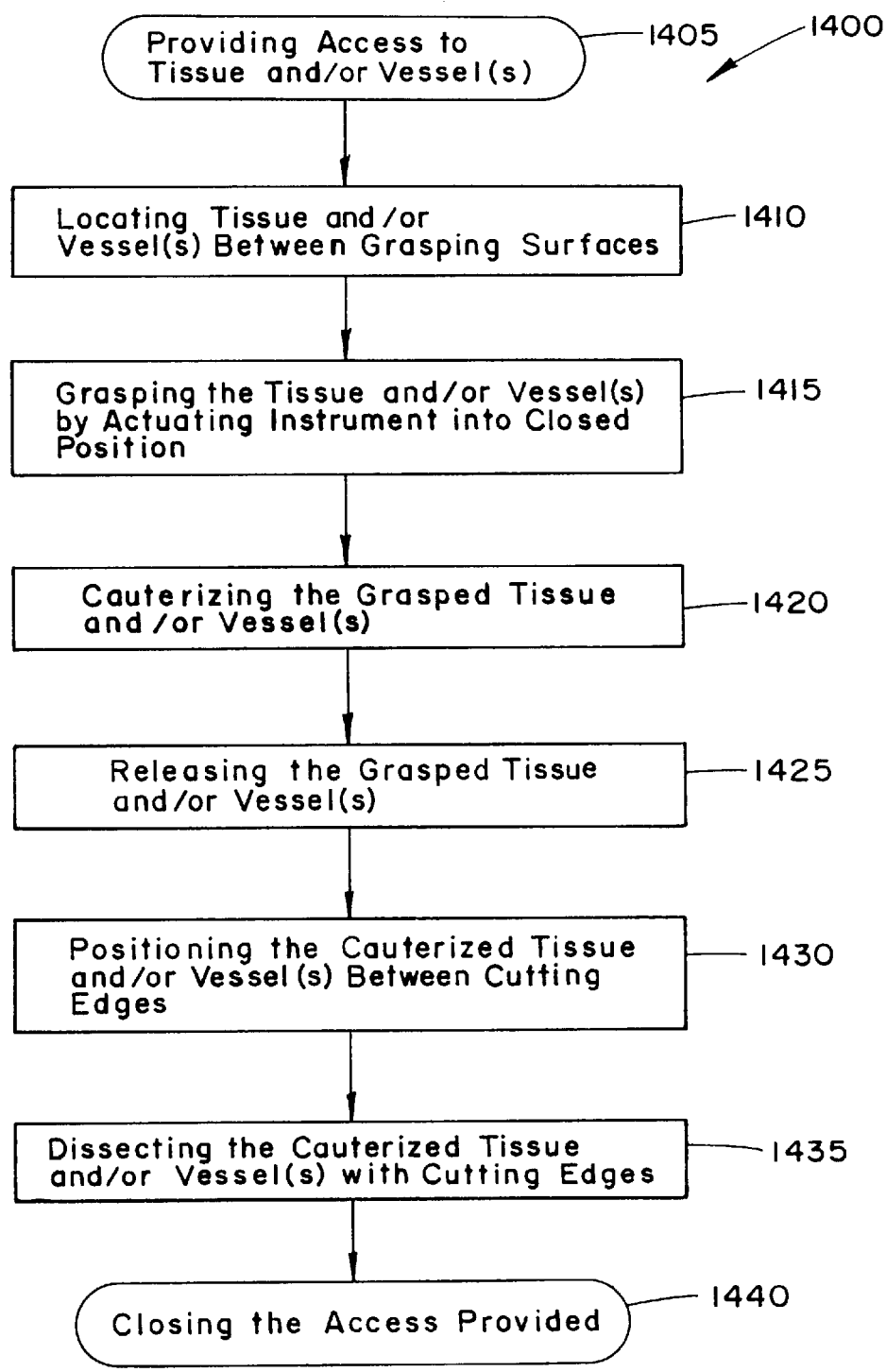
FIG. 14 illustrates the steps of a method utilizing an instrument of the present invention configured for open surgical procedures.

Referring now to FIG. 14, the steps outlining a method for using an open surgery version of the present invention are illustrated and referred to generally by reference numeral 1400. Access is first provided 1405 to the tissue and/or vessel(s) to be cauterized and dissected by exposing the interior of a body cavity. This is typically achieved by making a large incision through the skin and body wall. The tissue and/or vessel(s) to be cauterized and dissected are then located 1410. The located tissue and/or vessel(s) are grasped 1415 between the grasping surfaces of the instrument by actuating the instrument into a closed position.

The grasped tissue and/or vessel(s) are then cauterized 1420 by energizing the instrument with RF energy supplied by an electrosurgical generator 123. The instrument is then actuated into an open position thereby releasing 1425 the cauterized tissue and/or vessel(s). After releasing 1425, the cauterized tissue and/or vessel(s) are positioned 1430 between the cutting edges of the instrument. In the instrument 10 configured with the scissors portion distal to the graspers portion, as shown in FIG. 1A, positioning 1430 is accomplished by sliding the instrument backward from the grasping surfaces 20,22 to the cutting edges 16, 18. In the instrument 40 configured with the graspers portion distal to the scissors portion, as shown in FIG. 2A, positioning 1430 is accomplished by sliding the instrument forward from the grasping surfaces 20, 22 to the cutting edges 16,18.

The cauterized tissue and or vessel(s) are then dissected 1435 with the cutting edges 16,18 by actuating the instrument into a closed position. Lastly, the access provided 1405 is closed 1440 by any standard means known in the surgical arts.

Figure 15:
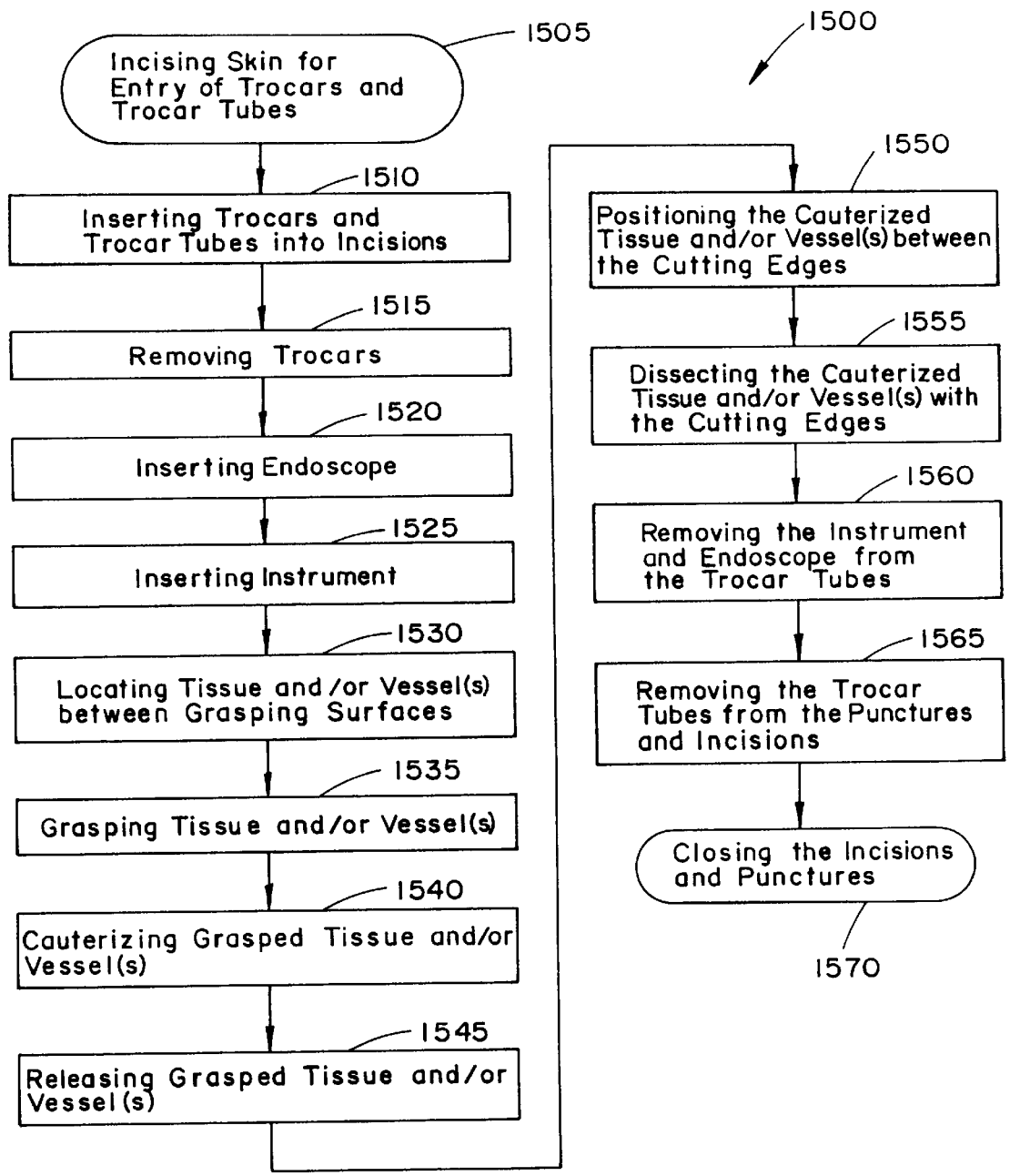
FIG. 15 illustrates the steps of a method utilizing an instrument of the present invention configured for endoscopic surgical procedures.

Referring now to FIG. 15, the steps outlining a method for using an endoscopic version of the present invention are illustrated and referred to generally by reference numeral 1500. Incisions 1505 are made through the patient's skin for facilitating the entry of trocars and trocar tubes. At least two trocar and trocar tube combinations are inserted 1510 through the body wall by puncturing the body wall to provide access to the tissue and/or vessel(s) to be cauterized and dissected in the body cavity. The trocars are removed 1515 leaving the trocar tubes in place providing access to the body cavity. An endoscope is inserted 1520 into a trocar tube providing a view of the body cavity on a monitor receiving video signals from the endoscope. An endoscopic version of the instrument of the present invention is then inserted 1525 into another trocar tube whereby its distal end is inside the body cavity and viewable on the video monitor. The tissue and/or vessel(s) to be cauterized and dissected are then located 1530. The located tissue and/or vessel(s) are grasped 1535 between the grasping surfaces of the instrument by actuating the instrument into a closed position.

The grasped tissue and/or vessel(s) are then cauterized 1540 by energizing the instrument with RF energy supplied by an electrosurgical generator 123. The instrument is then actuated into an open position thereby releasing 1545 the cauterized tissue and/or vessel(s). After releasing 1545, the cauterized tissue and/or vessel(s) are positioned 1550 between the cutting edges of the instrument. In the instrument 10 configured with the scissors portion distal to the graspers portion, as shown in FIG. 1A, positioning 1550 is accomplished by sliding the instrument backward from the grasping surfaces 20, 22 to the cutting edges 16, 18. In the instrument 40 configured with the graspers portion distal to the scissors portion, as shown in FIG. 2A, positioning 1550 is accomplished by sliding the instrument forward from the grasping surfaces 20, 22 to the cutting edges 16, 18.

The cauterized tissue and or vessel(s) are then dissected 1555 with the cutting edges 16,18 by actuating the instrument into a closed position. The instrument and endoscope are then removed 1560 from the trocar tubes. The trocar tubes are also removed 1565. Lastly, the incisions and punctures are closed 1570 by any standard means known in the surgical arts.

Of course, either the open or the surgical instrument of the present invention can be used solely as a grasper to coapt and coagulate already severed vessels or tissue. Likewise, the instruments of the present invention can also be used as a bipolar scissors to cut and coagulate smaller vessels, less than a few millimeters in diameter, that do not require precoagulation prior to cutting.

EXAMPLES

The following three open surgical procedures are examples of procedures which benefit from the instruments of the present invention.

1. Pericardiectomy for Constrictive Pericarditis

The pericardium is exposed through a midline sternal splitting incision. A small longitudinal incision is also made in the pericardium. An instrument of the present invention is then used to cauterize and incise the pericardium to remove the organized pericardial exudate and the pericardium. The instrument then cauterizes vessels of the pericardium prior to transection. The cauterization and transection are accomplished following the method steps discussed previously. Thoracic drains are placed and the edges of the sternum are approximated with encircling, interrupted stainless steel sutures. The fascia, subcutaneous tissue and skin are closed in a standard fashion.

2. Splenectomy

The peritoneal cavity is exposed through a left rectus paramedian, midline or subcostal incision. The spleen is displaced medially by manual manipulation. An instrument of the present invention is used to cauterize and transect the splenophrenic, splenorenal, and splenocolic ligaments. Short gastric vessels less than three millimeters in diameter are also cauterized and transected with an instrument of the present invention. The cauterization and transection are accomplished following the method steps discussed previously. Larger vessels are ligated and transected by any means known in the surgical arts. The splenic artery and vein are ligated and transected, and the spleen is excised. Lastly, the abdomen is closed in a standard fashion.

3. Harvesting For a Free Greater Omentum Transfer

An upper midline abdominal incision is made to expose the greater omentum. An instrument of the present invention is used to cauterize and transect short branches of the gastroepiploic arterial arch less than three millimeters in diameter which supply the greater curvature of the stomach. The cauterization and transection are accomplished following the method steps discussed previously. Larger vascular branches are ligated and transected. The omentum is separated from the transverse colon in a relatively avascular plane with an instrument of the present invention. The left gastroepiploic vessels are ligated and transected. The right gastroepiploic vessels are transected and a transplantation of the greater omentum performed. An end-to-side anastomosis of the gastroepiploic vessels is performed at the recipient site. Lastly, the midline abdominal incision is closed in a standard fashion.

From the foregoing, it becomes readily apparent to one skilled in the art that the novel combination bipolar scissors/ graspers instrument offers improved coaptation of vessels and decreases the number of instruments required in surgical procedures in which both cutting and grasping is required, which renders the instrument much more effective in certain surgical procedures and much less expensive to purchase, and to process in comparison with currently employed instruments.

Although this invention has been shown and described with respect to detailed embodiments thereof, it will be understood by those skilled in the art that various changes in form and detail thereof may be made without departing from the spirit and scope of the claimed invention.

What is claimed is:

1. A combination bipolar scissors and graspers surgical instrument comprising:

a first jaw member having a first cutting edge, a first cutting surface, and a first grasping surface, the first cutting edge being distal to the first grasping surface, the first jaw member further having a first pivoting surface;

a second jaw member having a second cutting edge and second cutting surface opposing the first cutting edge and first cutting surface, the second jaw member further having a second grasping surface opposing the first grasping surface and a second pivoting surface opposing the first pivoting surface and in sliding contact therewith;

a pivot pin pivotally connected to the jaw members wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position;

means for supplying electrical energy to the first jaw member and electrical energy of the opposite polarity to the second jaw member for cauterizing tissue therebetween;

isolating means for electrically isolating the first jaw member from the second jaw member; and actuation means for actuating the jaw members between their open and closed positions.

2. The instrument as claimed in claim 1, wherein the grasping surfaces are contained within the shape and size of standard scissor blades.

3. The instrument as claimed in claim 1, wherein each jaw member is individually pivotable in relation to the other jaw member about the pivot pin.

4. The instrument as claimed in claim 1, wherein the isolating means comprises:

an electrically insulating coating disposed on the first cutting surface such that the first cutting surface is electrically isolated from the second cutting surface when the jaw members are in their closed position but which allows electrical conduction between the first and second cutting edges when tissue is present therebetween;

means for maintaining an insulating gap between the first grasping surface and second grasping surface for permitting electrical conduction between the grasping surfaces when tissue is inserted therebetween but which prevents electrical conduction between the grasping surfaces when tissue is not present therebetween;

an electrically insulating coating disposed on one of the first or second pivoting surfaces; and means for preventing electrical conduction from the first jaw member to the second jaw member through the pivot pin.

5. The instrument as claimed in claim 4, wherein the means for maintaining an insulating gap comprises an electrically insulating coating disposed on the second grasping surface such that the first grasping surface is electrically isolated from the second grasping surface when the jaw members are in their closed position and tissue is not present therebetween, the electrically insulating coating being disposed on portions constituting less than the entire second grasping surface for permitting electrical conduction between the uncoated portions of the second grasping surface and the first grasping surface when the jaw members are in their closed position and tissue is present therebetween.

6. The instrument as claimed in claim 5, wherein the insulating coatings are aluminum oxide.

7. The instrument as claimed in claim 4, wherein the means for preventing electrical conduction from the first jaw member to the second jaw member through the pivot pin comprises an insulating coating disposed on the pivot pin.

8. The instrument as claimed in claim 4, wherein the means for preventing electrical conduction from the first jaw member to the second jaw member through the pivot pin comprises fabrication of the pivot pin fabricated from an insulating material.

9. The instrument as claimed in claim 8, wherein the insulating material is aluminum oxide.

10. The instrument as claimed in claim 8, wherein the insulating material is one of a polymer, a glass-filled polymer, and a ceramic-filled polymer.

11. The instrument as claimed in claim 1, wherein the actuating means comprises:

first and second elongated conductive members, each elongated member having a distal end and a proximal end, the first and second jaw members being integral with the distal ends of their respective elongated members; and a finger loop disposed on each of the proximal ends of the elongated members for actuating the jaw members between their open and closed positions.

12. The instrument as claimed in claim 11, wherein the means for supplying electrical energy to the jaw members comprises a first electrical connector disposed on the proximal end of the first elongated member and a second electrical connector disposed on the proximal end of the second elongated member for facilitating connection to an electrosurgical generator.

13. The instrument as claimed in claim 11 further comprising an insulating means for preventing electrical conduction from portions of the instrument other than the first and second jaw members and first and second electrical connectors.

14. The instrument as claimed in claim 13, wherein the insulating means comprises a nylon coating disposed on portions of the instrument other than substantially all of the first and second jaw members and first and second electrical connectors.

15. A combination bipolar scissors and graspers surgical instrument comprising:

a first jaw member having a first cutting edge, a first cutting surface, and a first grasping surface, the first grasping surface being distal to the first cutting edge, the first jaw member further having a first pivoting surface;

a second jaw member having a second cutting edge and second cutting surface opposing the first cutting edge and first cutting surface, the second jaw member further having a second grasping surface opposing the first grasping surface and a second pivoting surface opposing the first pivoting surface and in sliding contact therewith;

a pivot pin pivotally connected to the jaw members wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position;

means for supplying electrical energy to the first jaw member and electrical energy of the opposite polarity to the second jaw member for cauterizing tissue therebetween;

isolating means for electrically isolating the first jaw member from the second jaw member; and actuation means for actuating the jaw members between their open and closed positions;

wherein the isolating means comprises an electrically insulating coating disposed on the first cutting surface such that the first cutting surface is electrically isolated from the second cutting surface when the jaw members are in their closed position but which allows electrical conduction between the first and second cutting edges when tissue is present therebetween; means for maintaining an insulating gap between the first grassing surface and second grasping surface for permitting electrical conduction between the grasping surfaces when tissue is inserted therebetween but which prevents electrical conduction between the grasping surfaces when tissue is not present therebetween; an electrically insulating coating disposed on one of the first or second pivoting surfaces; and means for preventing electrical conduction from the first jaw member to the second jaw member through the pivot pin.

16. The instrument as claimed in claim 15, wherein each jaw member is individually pivotable in relation to the other jaw member about the pivot pin.

17. The instrument as claimed in claim 15, wherein the means for maintaining an insulating gap comprises an electrically insulating coating disposed on the second grasping surface such that the first grasping surface is electrically isolated from the second grasping surface when the jaw members are in their closed position and tissue is not present therebetween, the electrically insulating coating being disposed on portions constituting less than the entire second grasping surface for permitting electrical conduction between the uncoated portions of the second grasping surface and the first grasping surface when the jaw members are in their closed position and tissue is present therebetween.

18. The instrument as claimed in claim 17, wherein the insulating coatings are aluminum oxide.

19. The instrument as claimed in claim 15, wherein the means for preventing electrical conduction from the first jaw member to the second jaw member through the pivot pin comprises an insulating coating disposed on the pivot pin.

20. The instrument as claimed in claim 15, wherein the means for preventing electrical conduction from the first jaw member to the second jaw member through the pivot pin comprises fabrication of the pivot pin from an insulating material.

21. The instrument as claimed in claim 20, wherein the insulating material is aluminum oxide.

22. The instrument as claimed in claim 20, wherein the insulating material is one of a polymer, a glass-filled polymer, and a ceramic-filled polymer.

23. The instrument as claimed in claim 15, wherein the actuating means comprises:

first and second elongated conductive members, each elongated member having a distal end and a proximal end, the first and second jaw members being integral with the distal ends of their respective elongated members; and a finger loop disposed on each of the proximal ends of the elongated members for actuating the jaw members between their open and closed positions.

24. The instrument as claimed in claim 23, wherein the means for supplying electrical energy to the jaw members comprises a first electrical connector disposed on the proximal end of the first elongated member and a second electrical connector disposed on the proximal end of the second elongated member for facilitating connection to an electrosurgical generator.

25. The instrument as claimed in claim 24 further comprising an insulating means for preventing electrical conduction from portions of the instrument other than the first and second jaw members and first and second electrical connectors.

26. The instrument as claimed in claim 25, wherein the insulating means comprises a nylon coating disposed on portions of the instrument other than substantially all of the first and second jaw members and first and second electrical connectors.

27. A combination bipolar scissors and graspers surgical instrument comprising:

an elongated tube having a distal end, a proximal end, and a lumen;

a first jaw member pivotally disposed on the distal end of the elongated tube, the jaw member having a first cutting edge, a first cutting surface, and a first grasping surface, the first cutting edge being distal to the first grasping surface, the first jaw member further having a first pivoting surface;

a second jaw member pivotally disposed on the distal end of the elongated tube, the jaw member having a second cutting edge and second cutting surface opposing the first cutting edge and first cutting surface, the second jaw member further having a second grasping surface opposing the first grasping surface and a second pivoting surface opposing the first pivoting surface and in sliding contact therewith;

a pivot pin pivotally connected to the jaw members and fixed to the distal end of the elongated tube wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position;

means for supplying electrical energy to the first jaw member and electrical energy of the opposite polarity to the second jaw member for cauterization of tissue therebetween;

isolating means for electrically isolating the first jaw member from the second jaw member; and actuation means disposed on the proximal end of the elongated tube and coupled to the jaw members through the lumen of the elongated tube for actuating the jaws members between their open and closed positions.

28. The instrument as claimed in claim 27, wherein the grasping surfaces are contained within the shape and size of standard scissor blades.

29. The instrument as claimed in claim 27, wherein each jaw member is individually pivotable in relation to the other jaw member about the pivot pin.

30. The instrument as claimed in claim 27, wherein the isolating means comprises:

an electrically insulating coating disposed on the first cutting surface such that the first cutting surface is electrically isolated from the second cutting surface when the jaw members are in their closed position but which allows electrical conduction between the first and second cutting edges when tissue is present therebetween;

means for maintaining an insulating gap between the first grasping surface and second grasping surface for permitting electrical conduction between the grasping surfaces when tissue is inserted therebetween but which prevents electrical conduction between the grasping surfaces when tissue is not present therebetween;

an electrically insulating coating disposed on one of the first or second pivoting surfaces; and means for preventing electrical conduction from the first jaw member to the second jaw member through the pivot pin.

31. The instrument as claimed in claim 30, wherein the means for maintaining an insulating gap comprises an electrically insulating coating disposed on the second grasping surface such that the first grasping surface is electrically isolated from the second grasping surface when the jaw members are in their closed position and tissue is not present therebetween, the electrically insulating coating being disposed on portions constituting less than the entire second grasping surface for permitting electrical conduction between the uncoated portions of the second grasping surface and the first grasping surface when the jaw members are in their closed position and tissue is present therebetween.

32. The instrument as claimed in claim 31, wherein the insulating coatings are aluminum oxide.

33. The instrument as claimed in claim 30, wherein the means for preventing electrical conduction from the first jaw member to the second jaw member through the pivot pin comprises an insulating coating disposed on the pivot pin.

34. The instrument as claimed in claim 30, wherein the means for preventing electrical conduction from the first jaw member to the second jaw member through the pivot pin comprises fabrication of the pivot pin from an insulating material.

35. The instrument as claimed in claim 34, wherein the insulating material is aluminum oxide.

36. The instrument as claimed in claim 34, wherein the insulating material is one of a polymer, a glass-filled polymer, and a ceramic-filled polymer.

37. The instrument as claimed in claim 27, wherein the actuation means comprises:
a first handle member secured to the proximal end of the elongated tube;
a second handle member pivotally connected to the first handle member;
a wire member having a distal end and a proximal end disposed in the lumen of the elongated tube, the proximal end of the wire member being fastened to the second handle member; and
a coupling means for coupling the distal end of the wire member to the jaw members such that the jaw members are actuated when the second handle member is pivoted about the first handle member.

38. The instrument as claimed in claim 37, wherein the means for supplying electrical energy to the jaw members comprises a power cord disposed on the first handle member for connection to an electrosurgical generator, the power cord having a first and second insulated lead, the first insulated lead carrying electrical energy of a certain polarity, the second insulated lead carrying electrical energy of an opposite polarity, the first and second leads extending through the lumen of the elongated tube and being electrically connected to their respective first and second jaw members for supplying electrical energy of opposite polarities to the jaw members.

39. The instrument as claimed in claim 37 further comprising an insulating means for preventing electrical conduction from portions of the instrument other than the first and second jaw members.

40. The instrument as claimed in claim 39, wherein the insulating means comprises an insulating coating disposed on the elongated tube and wherein the first and second handle members are fabricated from a non-conductive material.

41. A method for using the bipolar combination scissors and graspers instrument as claimed in claims 1 or 27, the method comprising the steps of:
providing access to the tissue and/or vessel(s) to be cauterized and dissected by exposing the interior of a body cavity;
locating the tissue and/or vessel(s) to be cauterized and dissected between the grasping surfaces of the instrument;
grasping the tissue and/or vessel(s) by actuating the instrument into a closed position;
cauterizing the grasped tissue and/or vessel(s) by energizing the instrument with RF energy supplied by an electrosurgical generator;
releasing the grasped tissue and/or vessel(s) by actuating the instrument into an open position;
positioning the cauterized tissue and/or vessel(s) between the cutting edges of the instrument by sliding the instrument backward from the grasping surfaces to the cutting edges;
dissecting the cauterized tissue and or vessel(s) with the cutting edges by actuating the instrument into a closed position; and
closing the access provided to the cauterized and dissected tissue and/or vessel(s).

42. A combination bipolar scissors and graspers surgical instrument comprising:
an elongated tube having a distal end, a proximal end, and a lumen;
a first jaw member pivotally disposed on the distal end of the elongated tube, the jaw member having a first cutting edge, a first cutting surface, and a first grasping surface, the first grasping surface being distal to the first cutting edge, the first jaw member further having a first pivoting surface;
a second jaw member pivotally disposed on the distal end of the elongated tube, the jaw member having a second cutting edge and second cutting surface opposing the first cutting edge and first cutting surface, the second jaw member further having a second grasping surface opposing the first grasping surface and a second pivoting surface opposing the first pivoting surface and in sliding contact therewith;
a pivot pin pivotally connected to the jaw members and fixed to the distal end of the elongated tube wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position;
means for supplying electrical energy to the first jaw member and electrical energy of the opposite polarity to the second jaw member for cauterization of tissue therebetween;
isolating means for electrically isolating the first jaw member from the second jaw member; and
actuation means disposed on the proximal end of the elongated tube and coupled to the jaw members through the lumen of the elongated tube for actuating the jaws members between their open and closed positions;
wherein the isolating means comprises an electrically insulating coating disposed on the first cutting surface such that the first cutting surface is electrically isolated from the second cutting surface when the jaw members are in their closed position but which allows electrical conduction between the first and second cutting edges when tissue is present therebetween; means for maintaining an insulating gap between the first grasping surface and second grasping surface for permitting electrical conduction between the grasping surfaces when tissue is inserted therebetween but which prevents electrical conduction between the grasping surfaces when tissue is not present therebetween; an electrically insulating coating disposed on one of the first or second pivoting surfaces; and means for preventing electrical conduction from the first jaw member to the second jaw member through the pivot pin.

43. The instrument as claimed in claim 42, wherein each jaw member is individually pivotable in relation to the other jaw member about the pivot pin.

44. The instrument as claimed in claim 42, wherein the means for maintaining an insulating gap comprises an electrically insulating coating disposed on the second grasping surface such that the first grasping surface is electrically isolated from the second grasping surface when the jaw members are in their closed position and tissue is not present therebetween, the electrically insulating coating being disposed on portions constituting less than the entire second grasping surface for permitting electrical conduction between the uncoated portions of the second grasping surface and the first grasping surface when the jaw members are in their closed position and tissue is present therebetween.

45. The instrument as claimed in claim 44, wherein the insulating coatings are aluminum oxide.

46. The instrument as claimed in claim 42, wherein the means for preventing electrical conduction from the first jaw member to the second jaw member through the pivot pin comprises an insulating coating disposed on the pivot pin.

47. The instrument as claimed in claim 42, wherein the means for preventing electrical conduction from the first jaw member to the second jaw member through the pivot pin comprises fabrication of the pivot pin from an insulating material.

48. The instrument as claimed in claim 47, wherein the insulating material is aluminum oxide.

49. The instrument as claimed in claim 47, wherein the insulating material is one of a polymer, a glass-filled polymer, and a ceramic-filled polymer.

50. The instrument as claimed in claim 42, wherein the actuation means comprises:
- a first handle member secured to the proximal end of the elongated tube;
- a second handle member pivotally connected to the first handle member;
- a wire member having a distal end and a proximal end disposed in the lumen of the elongated tube, the proximal end of the wire member being fastened to the second handle member; and
- coupling means for coupling the distal end of the wire member to the jaw members such that the jaw members are actuated when the second handle member is pivoted about the first handle member.

51. The instrument as claimed in claim 50, wherein the means for supplying electrical energy to the jaw members comprises a power cord disposed on the first handle member for connection to an electrosurgical generator, the power cord having a first and second insulated lead, the first insulated lead carrying electrical energy of a certain polarity, the second insulated lead carrying electrical energy of an opposite polarity, the first and second leads extending through the lumen of the elongated tube and being electrically connected to their respective first and second jaw members for supplying electrical energy of opposite polarities to the jaw members.

52. The instrument as claimed in claim 50 further comprising an insulating means for preventing electrical conduction from portions of the instrument other than the first and second jaw members.

53. The instrument as claimed in claim 52, wherein the insulating means comprises an insulating coating disposed on the elongated member and wherein the first and second handle members are fabricated from a non-conductive material.

* * * * *